US009320451B2

(12) United States Patent
Feldkamp et al.

(10) Patent No.: US 9,320,451 B2
(45) Date of Patent: Apr. 26, 2016

(54) METHODS FOR ASSESSING HEALTH CONDITIONS USING SINGLE COIL MAGNETIC INDUCTION TOMOGRAPHY IMAGING

(71) Applicant: Kimberly-Clark Worldwide, Inc., Neenah, WI (US)

(72) Inventors: Joseph R. Feldkamp, Appleton, WI (US); Shawn Jeffery Sullivan, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 168 days.

(21) Appl. No.: 14/191,967

(22) Filed: Feb. 27, 2014

(65) Prior Publication Data
US 2015/0238114 A1    Aug. 27, 2015

(51) Int. Cl.
*A61B 5/05* (2006.01)
*A61B 5/00* (2006.01)

(52) U.S. Cl.
CPC ............. *A61B 5/0522* (2013.01); *A61B 5/7425* (2013.01)

(58) Field of Classification Search
CPC .......................... A61B 5/0522; A61B 5/7425
See application file for complete search history.

(56) References Cited

U.S. PATENT DOCUMENTS

| 5,144,236 | A | 9/1992 | Strenk | |
|---|---|---|---|---|
| 5,644,319 | A * | 7/1997 | Chen | H01Q 9/0421 343/702 |
| 5,818,232 | A | 10/1998 | Mehr et al. | |
| 6,590,394 | B2 * | 7/2003 | Wong | G01R 33/341 324/318 |
| 6,865,494 | B2 | 3/2005 | Duensing et al. | |
| 7,839,147 | B2 | 11/2010 | Katscher et al. | |
| 7,923,995 | B2 | 4/2011 | Schulz | |
| 8,115,488 | B2 | 2/2012 | McDowell | |
| 8,125,220 | B2 | 2/2012 | Igney et al. | |
| 8,384,378 | B2 | 2/2013 | Feldkamp et al. | |
| 8,423,129 | B2 | 4/2013 | Waffenschmidt et al. | |
| 8,452,388 | B2 | 5/2013 | Feldkamp et al. | |
| 8,725,245 | B2 | 5/2014 | Feldkamp et al. | |
| 8,812,078 | B2 * | 8/2014 | Vernickel | A61B 5/05 324/300 |

(Continued)

FOREIGN PATENT DOCUMENTS

| CN | 102499681 | 6/2012 |
|---|---|---|
| CN | 102499682 | 6/2012 |

(Continued)

OTHER PUBLICATIONS

Feldkamp et al., "Effects of Extremity Elevation and Health Factors on Soft Tissue Electrical Conductivity", Measurement Science Review, vol. 9, No. 6, Jan. 2009, pp. 169-178.

(Continued)

*Primary Examiner* — Dixomara Vargas
(74) *Attorney, Agent, or Firm* — Dority & Manning, P.A.

(57) ABSTRACT

Methods for assessing a health condition of an individual using single coil magnetic induction tomography imaging are provided. A target area for medical imaging on a patient can be identified. A plurality of coil property measurements can be obtained using a single coil. The plurality of coil property measurements can be performed with the single coil at a plurality of discrete locations relative to the target area. The coil property measurements can be processed to generate an image of the conductivity distribution of the target area. The image can be analyzed to assess a health condition of the patient.

22 Claims, 10 Drawing Sheets

(56) References Cited

U.S. PATENT DOCUMENTS

| | | | |
|---|---|---|---|
| 2004/0079485 A1 | 4/2004 | Lee et al. | |
| 2004/0124779 A1 | 7/2004 | Howald et al. | |
| 2005/0088179 A1 | 4/2005 | Sato | |
| 2006/0125475 A1* | 6/2006 | Sodickson | A61B 5/0536 324/300 |
| 2008/0258717 A1 | 10/2008 | Igney et al. | |
| 2009/0102480 A1 | 4/2009 | Katscher et al. | |
| 2009/0219289 A1 | 9/2009 | Kalvin | |
| 2010/0127705 A1 | 5/2010 | Scharfetter | |
| 2010/0182005 A1 | 7/2010 | Biber | |
| 2011/0004432 A1 | 1/2011 | Chen et al. | |
| 2011/0007937 A1 | 1/2011 | Yan et al. | |
| 2011/0133729 A1 | 6/2011 | Vernickel et al. | |
| 2011/0133731 A1 | 6/2011 | Vauhkonen et al. | |
| 2011/0172512 A1 | 7/2011 | Yan et al. | |
| 2011/0282609 A1 | 11/2011 | Liu et al. | |
| 2011/0313277 A1 | 12/2011 | Igney et al. | |
| 2012/0019238 A1 | 1/2012 | Eichardt et al. | |
| 2012/0101773 A1 | 4/2012 | Mcewan et al. | |
| 2012/0126800 A1* | 5/2012 | Vernickel | A61B 5/05 324/234 |
| 2012/0150458 A1 | 6/2012 | Sodickson et al. | |
| 2012/0153943 A1 | 6/2012 | Jin et al. | |
| 2012/0161782 A1 | 6/2012 | Ross | |
| 2012/0169333 A1 | 7/2012 | Katscher et al. | |
| 2015/0035533 A1 | 2/2015 | Lips et al. | |
| 2015/0238114 A1 | 8/2015 | Feldkamp et al. | |
| 2015/0241372 A1* | 8/2015 | Feldkamp | G01N 27/023 702/65 |
| 2015/0241373 A1* | 8/2015 | Feldkamp | G01N 27/023 324/654 |

FOREIGN PATENT DOCUMENTS

| | | |
|---|---|---|
| CN | 103033847 | 4/2013 |
| EP | 2332463 | 6/2011 |
| EP | 2333587 | 6/2011 |
| JP | 2005-124692 | 5/2005 |
| RU | 2129406 | 4/1999 |
| WO | 2004-026136 A1 | 4/2004 |
| WO | 2005057467 | 6/2005 |
| WO | 2009138934 | 11/2009 |
| WO | 2009/144461 | 12/2009 |
| WO | 2010003162 | 1/2010 |
| WO | 2010023586 | 3/2010 |
| WO | 2010052609 | 5/2010 |
| WO | 2010097726 | 9/2010 |
| WO | 2011161571 | 12/2011 |
| WO | 2012104799 | 8/2012 |

OTHER PUBLICATIONS

Gabriel et al., "The Dielectric Properties of Biological Tissues: I. Literature Survey", Physics in Medicine and Biology, vol. 41, No. 11, Nov. 1996, pp. 2231-2249.

Gonzalez et al., "Volumetric Electromagnetic Phase-Shift Spectroscopy of Brain Edema and Hematoma", PloS ONE, vol. 8, Issue 5, May 14, 2013, 10 pages.

Guardo et al., "Contactless Measurement of Thoracic Conductivity Changes by Magnetic Induction", Proceedings of the 19th International Conference IEEE/EMBS, vol. 6, Oct. 30-Nov. 2, 1997, Chicago, Illinois, pp. 2450-2453.

Haemmerich et al., "In Vivo Electrical Conductivity of Hepatic Tumours", Physiological Measurement, vol. 24, No. 2, May 2003, pp. 251-260

Harpen et al., "Influence of Skin Depth on NMR Coil Impedance, Part II", Physics in Medicine and Biology, vol. 33, No. 5, May 1988, pp. 597-605.

Lionheart et al., Sensitivity Analysis of 3D Magnetic Induction Tomography (MIT), $3^{rd}$ World Congress on Industrial Process Tomography, Sep. 2-5, 2003, Banff, Alberta, Canada, pp. 239-244.

Luis et al., "Magnetic Inductance Tomography Imaging Using Tikhonov Regularization", Workshop on Inverse Obstacle Problems, Nov. 4-6, 2002, Lisbon, Portugal, 4 pages.

Netz et al., "Contactless Impedance Measurement by Magnetic Induction—A Possible Method for Investigation of Brain Impedance", Physiological Measurement, vol. 14, No. 4, Nov. 1993, pp. 463-471.

Puwal et al., "Fourier-Based Magnetic Induction Tomography for Mapping Resistivity", Journal of Applied Physics, vol. 109, No. 1, Jan. 1, 2011, pp. 014701-1-014701-5.

Soleimani et al., "Forward Problem in 3D Magnetic Induction Tomography (MIT)", $3^{rd}$ World Congress on Industriai Process Tomography, Sep. 2-5, 2003, Banff, Alberta, Canada, pp. 275-280.

Wei et al., "Electromagnetic Tomography for Medical and Industrial Applications: Challenges and Opportunities", Proceedings of the IEEE, vol. 101, No. 3, Mar. 2013, pp. 559-565.

Wei et al., "Three-Dimensional Magnetic Induction Tomography Imaging Using a Matrix Free Krylov Subspace Inversion Algorithm", Progress in Electromagnetics Research, vol. 122, Jan. 2012, pp. 29-45.

Zaman et al., "The Impedance of a Single-Turn Coil Near a Conducting Half Space", Journal of Nondestructive Evaluation, vol. 1, No. 3, Aug. 1980, pp. 183-189.

PCT International Search Report for corresponding PCT Application No. PCT/IB2014/063154, mailed on Dec. 8, 2014, 4 pages.

* cited by examiner

METHODS FOR ASSESSING HEALTH CONDITIONS USING SINGLE COIL MAGNETIC INDUCTION TOMOGRAPHY IMAGING

FIELD OF THE INVENTION

The present disclosure relates generally to methods for assessing human health conditions using medical imaging and more particularly to assessing human health conditions using single coil magnetic induction tomography imaging.

BACKGROUND

Medical imaging technologies can be used to assess various health conditions of patients. Medical imaging technologies can vary widely in cost and portability, ranging from relatively inexpensive ultrasound to more costly methods such as computed tomography (CT) scans and magnetic resonance imaging (MRI). The portability of CT and MRI imaging systems is limited, making access to such imaging technology difficult for certain members of the population and in certain circumstances. While ultrasound technology is relatively inexpensive and portable, its use can be limited when either bone or gases obscure the target area of interest.

Magnetic induction tomography imaging can be used to image electromagnetic property distributions (e.g. conductivity or permittivity) within human tissues. More particularly, magnetic induction tomography techniques can provide for the low cost, contactless measurement of electromagnetic properties of human tissue based on eddy currents induced in tissues by induction coils placed adjacent to the tissue. Existing techniques for magnetic induction tomography imaging typically involve the placement of a large number of coils (e.g. a coil array) near the sample and building an image based upon the measured mutual inductance of coil pairs within the large number of coils placed near the specimen. For instance, an array of source coils and an array of detection coils can be placed adjacent the specimen. One or more of the source coils can be energized using radiofrequency energy and a response can be measured at the detection coils. The conductivity distribution (or permittivity distribution) of the specimen can be determined from the response of the detection coils.

SUMMARY

Aspects and advantages of embodiments of the present disclosure will be set forth in part in the following description, or may be learned from the description, or may be learned through practice of the embodiments.

One example aspect of the present disclosure is directed to a method for assessing a health condition of a patient. The method includes identifying a target area on a patient for medical imaging and obtaining a plurality of coil property measurements of the target area using a single coil. The plurality of coil property measurements are performed with the single coil at a plurality of discrete locations relative to the target area. The method further includes processing the plurality of coil property measurements to generate an image of the conductivity distribution of the target area. The method further includes outputting the image for assessment of a health condition of the patient.

Variations and modifications can be made to this example aspect and other aspects of the present disclosure.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussions of embodiments directed to one of ordinary skill in the art are set forth in the specification, which makes reference to the appended figures, in which.

DETAILED DESCRIPTION

Figure 1:
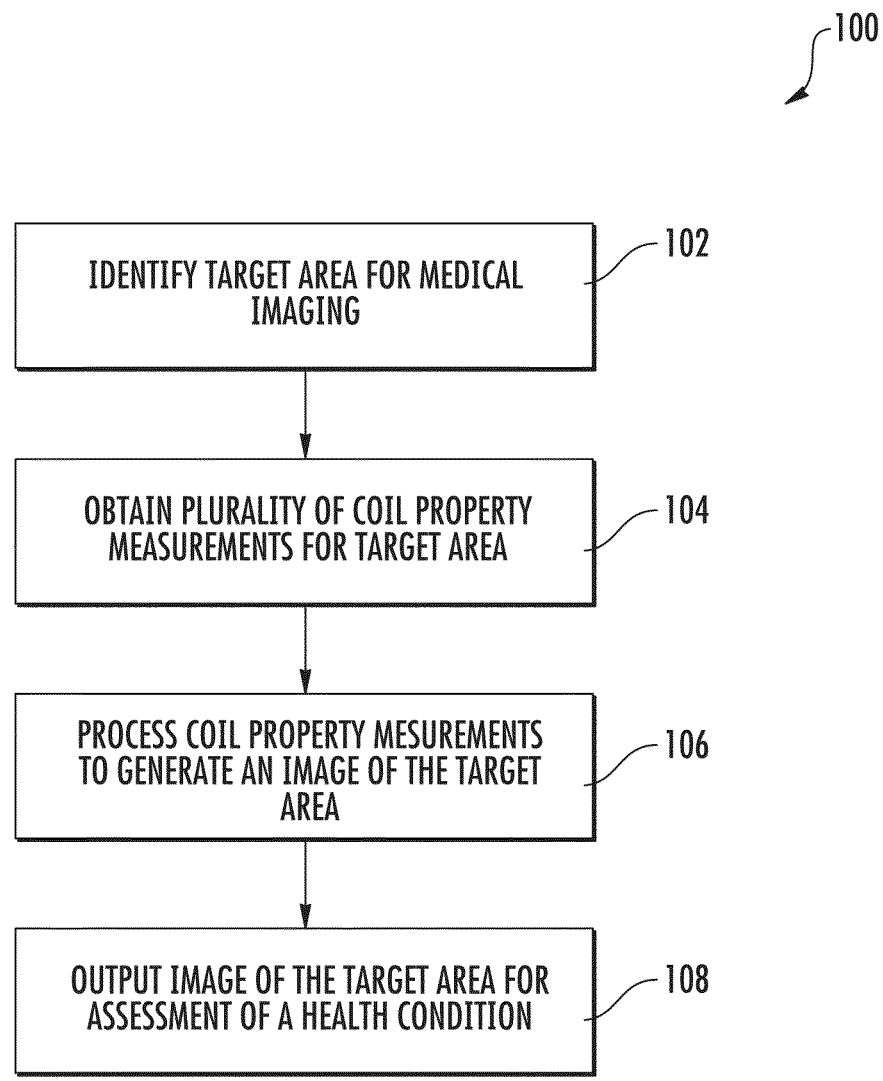
FIG. 1 depicts a flow diagram of an example method for assessing a health condition of a patient according to example embodiments of the present disclosure.

Reference now will be made in detail to embodiments, one or more examples of which are illustrated in the drawings. Each example is provided by way of explanation of the embodiments, not limitation of the invention. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Overview

Generally, example aspects of the present disclosure are directed to methods for assessing health conditions with magnetic induction tomography imaging using a single coil. Existing medical imaging technologies, such as CT scans and MRI imaging technologies, can be expensive and can be difficult to access for certain members of the population (e.g. the rural population or soldiers in combat situations). Ultrasound imaging technology can provide a cheaper and more readily available (e.g. portable) alternative to CT scans and MRI imaging technologies. However, the use of ultrasound technology can be limited, for instance, when bone or gases obscure the target area of interest.

Magnetic induction tomography imaging can provide a low cost solution for medical imaging of a patient. Electromagnetic properties, such as conductivity and permittivity, vary spatially in biomedical tissue due to natural contrasts created by fat, bone, muscle and various organs. As a result, a conductivity or permittivity distribution obtained using magnetic induction tomography imaging techniques can be used to image various regions of the body, including lungs and abdominal regions, brain tissue, spinal column, and other regions of the body that may or may not be difficult to image using other imaging techniques, such as ultrasound.

Typical existing magnetic induction tomography systems use a plurality of coils (e.g. an array of source coils and an array of detection coils) to generate conductivity maps. The use of multiple coils increases the complexity of magnetic induction tomography systems, leading to increased costs and reduced portability of the systems. This can result in reduced accessibility of the magnetic induction tomography imaging systems, for instance in rural areas.

Example aspects of the present disclosure are directed to methods of assessing health conditions of a human (or other biological entity) with magnetic induction tomography using a single coil. More particularly, a target area on a patient can be identified for medical imaging. The target area can include any suitable location on the patient, such as a location that may be at least partially obscured by bone tissue or at least partially obscured by a gas. A plurality of coil property measurements can be obtained for the target area using the single coil at a plurality of different discrete locations relative to the target area.

The plurality of coil property measurements can be performed with the single coil in a variety of ways. For instance, in one implementation, a patient can press the target area (e.g. a breast) against a non-conductive plate. A single coil disposed on the other side of the non-conductive plate can obtain a plurality of coil property measurements at a plurality of discrete locations relative to the non-conductive plate. As another example, a patient can be required to lie down on a non-conductive table in either a supine or prone position, while optional additional non-conductive supports assist in keeping the target area(s) of the patient motionless. A single coil can be disposed within a cavity in the non-conductive table underlying the patient. The single coil can be positioned (e.g. by a translation device) and controlled to perform a plurality of coil property measurements at a plurality of discrete locations relative to a target area. As yet another example, the plurality of coil property measurements can be obtained by a medical professional using a hand held device containing the single coil. The medical professional can position the single coil relative to the patient in accordance with indicia presented on one or more layers of non-conductive sheets overlaying the patient.

A three-dimensional electromagnetic property map, such as a three-dimensional conductivity map or a three-dimensional permittivity map, can be generated from the plurality of coil property measurements obtained using the single coil. More particularly, the present inventors have discovered a model that defines a relationship between coil loss measurements obtained using a single coil and an electromagnetic property distribution of a specimen. In one implementation, the model is a quantitative analytical model that describes the real part of a change in impedance (e.g. ohmic loss) of a single planar multi-loop coil, having a plurality of concentric conductive loops, resulting from induced eddy currents when excited with RF energy and placed near to arbitrarily shaped objects with arbitrary three-dimensional conductivity distributions.

Using the model, a three-dimensional electromagnetic property map can be generated for the target area from the plurality of coil property measurements obtained using the single coil. One or more images of the target area can be generated from the three-dimensional electromagnetic property map. For instance, an image of the conductivity distribution of the target area can be generated. The one or more images can be output on an output device (e.g. printed by a printer, presented on a display device, etc.) for examination by a medical professional. The images can be analyzed by the medical professional to assess a variety of health conditions of the patient, such as identification of cancerous tissues, assessing burn conditions, assessing peripheral artery disease, and assessing other health conditions.

Example Methods for Assessing a Health Condition

FIG. 1 depicts a process flow diagram of an example method (100) for assessing a health condition using single coil magnetic induction tomography imaging techniques according to example embodiments of the present disclosure. FIG. 1 depicts steps performed in a particular order for purposes of illustration and discussion. Those of ordinary skill in the art, using the disclosures provided herein, will understand that the steps of any of the methods disclosed herein can be modified, omitted, rearranged, adapted, or expanded in various ways without deviating from the scope of the present disclosure.

At (102), the method includes identifying a target area of a patient for medical imaging. Identifying the target area can include receiving instructions for imaging a particular area or location of a patient. While the present disclosure will be discussed with reference to imaging a target area of a human patient for example purposes, those of ordinary skill in the art, using the disclosures provided herein will understand that the aspects of the present disclosure are applicable to other biomedical imaging applications (e.g. veterinary imaging applications).

The target area can be any suitable portion of the patient desired to be imaged. In particular implementations, the target area can include portions of the patient that are difficult to image using other imaging techniques, such as ultrasound. More particularly, at least a portion of the target area can be obscured by bone tissue. For instance, the target area can include a portion of brain tissue beneath the skull of the patient or a spinal cord beneath the vertebrae of the patient. As another example, at least a portion of the target area can be occupied by a gas. For instance, the target area can include one or more of the trachea, lungs, stomach, bowels, pancreas, or other abdominal regions of the patient.

Figure 7:
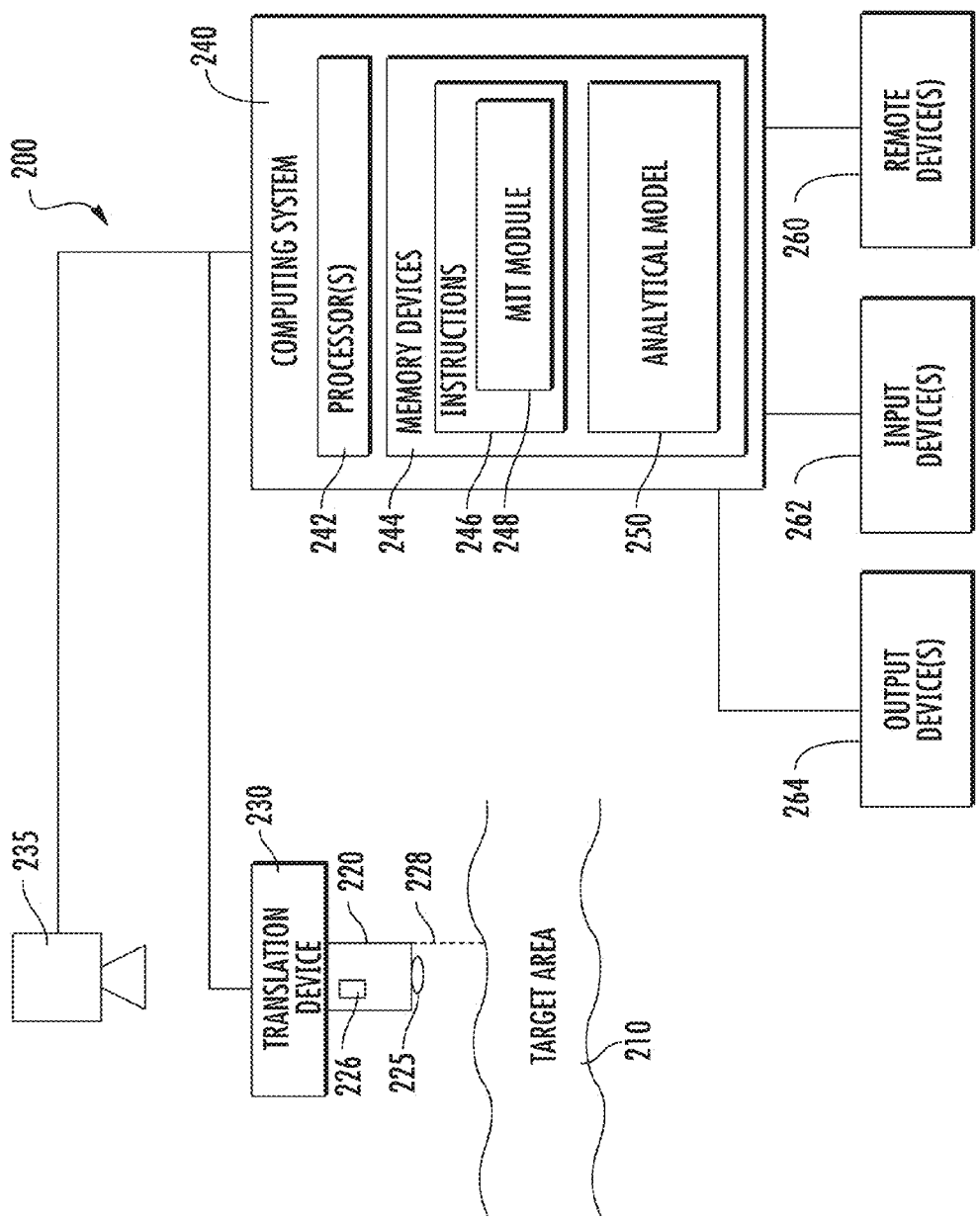
FIG. 7 depicts an example system for magnetic induction tomography imaging using a single coil according to example embodiments of the present disclosure.

Referring back to FIG. 1 at (104), a plurality of coil property measurements can be obtained using a single coil of a magnetic induction tomography imaging system, such as the system 200 in FIG. 7. As used herein, obtaining the plurality of coil property measurements can include accessing the coil property measurements stored, for instance, in a memory, receiving the coil property measurements, and/or actually performing the coil property measurements using a single coil. The coil property measurements can include, for instance, coil loss measurements indicative of a change in impedance of the single coil resulting from eddy currents induced in the target area when the single coil is placed adjacent to the target area and energized with radio frequency energy. The single coil can include a plurality of concentric conductive loops arranged in one or more planes on a printed circuit board.

The coil property measurements can be performed for the target area using the single coil at a plurality of discrete locations relative to the target area. Position data can be associated with each coil property measurement for use in generating an image of the target area. The coil property measurements can be performed for a plurality of discrete locations relative to the target area of the patient in a variety of manners.

Figure 2:
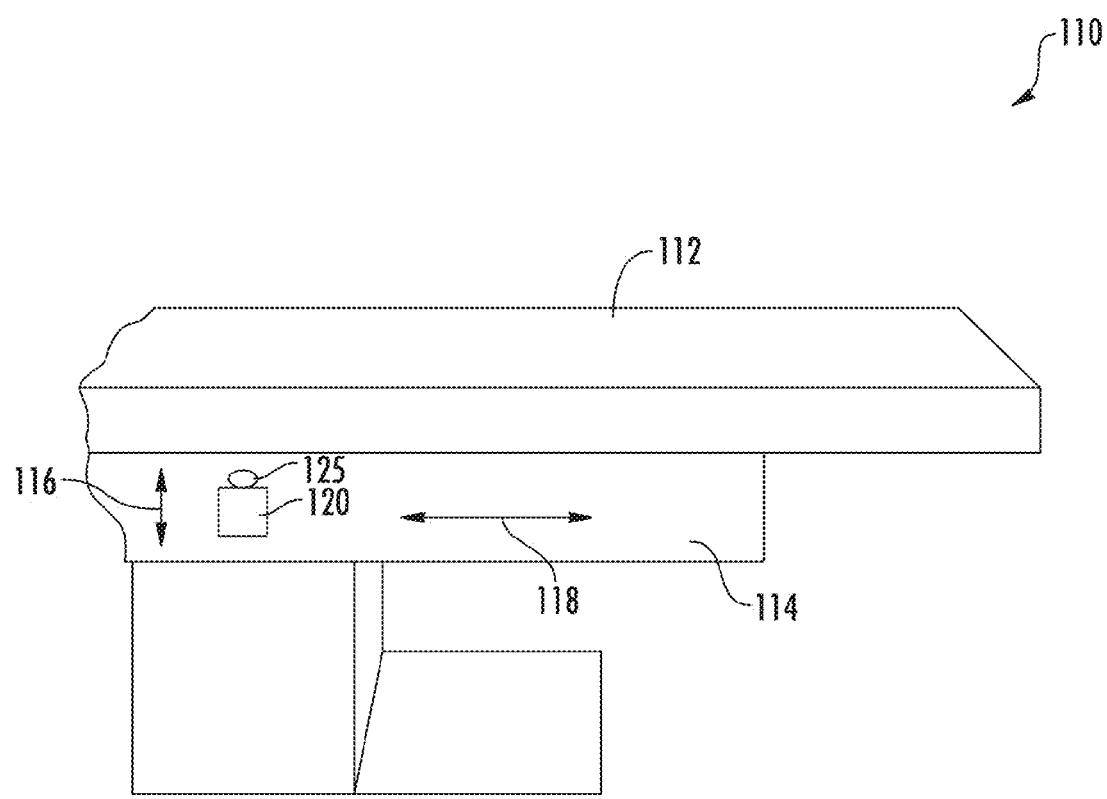
FIG. 2 depicts an example medical examination table that can be used to perform a plurality of coil property measurements with a single coil at a plurality of discrete locations relative to the target area according to example embodiments of the present disclosure.

For example, FIG. 2 depicts an example medical examination table 110 that can be used to perform a plurality of coil property measurements with a single coil at a plurality of discrete locations relative to the target area. The medical examination table 110 can include a non-conductive upper surface 112. A patient can be directed to lie down on the upper surface 112 in one of a variety of positions, such as a prone position or a supine position. The surface 112 helps to mechanically stabilize the body surface of the patient, in addition to any other non-conductive supporting structures that may help to immobilize and localize the target area(s). The medical examination table 110 can include a cavity 114 disposed underneath the surface 112. A coil device 120 can be located within the cavity 114. The coil device 120 can include a single coil 125 configured according to example aspects of the present disclosure, such as the coil 300 depicted in FIG. 8. Referring to FIG. 2, a translation device (not shown in FIG. 2) can be configured to move the coil device 120 in the directions indicated by arrows 116 and 118 to perform a plurality of coil property measurements with the single coil 125 at a plurality of discrete locations relative to the target area of the patient.

Figure 3:
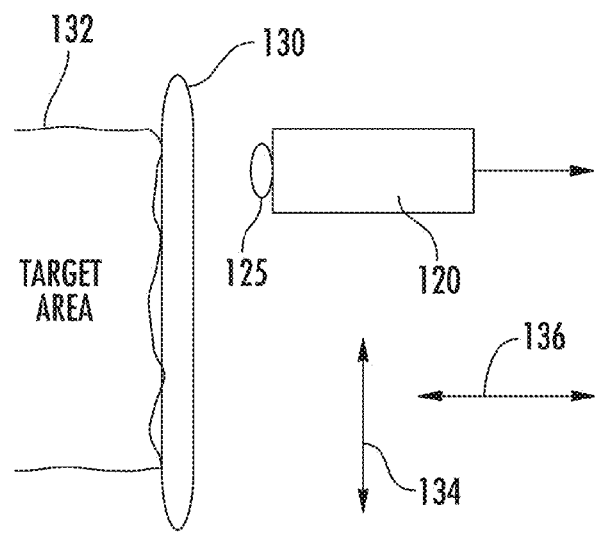
FIG. 3 depicts an example non-conductive plate that can be used to perform a plurality of coil property measurements with a single coil at a plurality of discrete locations relative to the target area according to example embodiments of the present disclosure.

FIG. 3 depicts an example non-conductive plate 130 for performing a plurality of coil property measurements with a single coil at a plurality of discrete locations relative to the target area. More particularly, a patient can be directed to press at least a portion of a target area 132 (e.g. a breast) against one surface of a non-conductive plate 130, or the surface of the non-conductive plate 130 can be shaped so as to accommodate and immobilize the target area 132 (e.g. a breast) in a more comfortable manner. A coil device 120 can be disposed on the other side of the non-conductive surface 130. The coil device 120 can include a single coil 125 configured according to example aspects of the present disclosure, such as the coil 300 depicted in FIG. 8. Referring to FIG. 2, a translation device (not shown in FIG. 2) can be configured to move the coil device 120 in the directions indicated by arrows 134 and 136 to perform a plurality of coil property measurements with the single coil 125 at a plurality of discrete locations relative to the target area of the patient.

According to other example aspects of the present disclosure, the plurality of coil property measurements can be manually performed by a medical professional using a hand held coil device having a single coil configured according to example aspects of the present disclosure. Accurate position data needs to be obtained for coil property measurements manually performed by a medical professional. Example techniques for obtaining accurate position data will be discussed in more detail below with reference to the example magnetic induction tomography imaging system 200 of FIG. 7.

Figure 4:
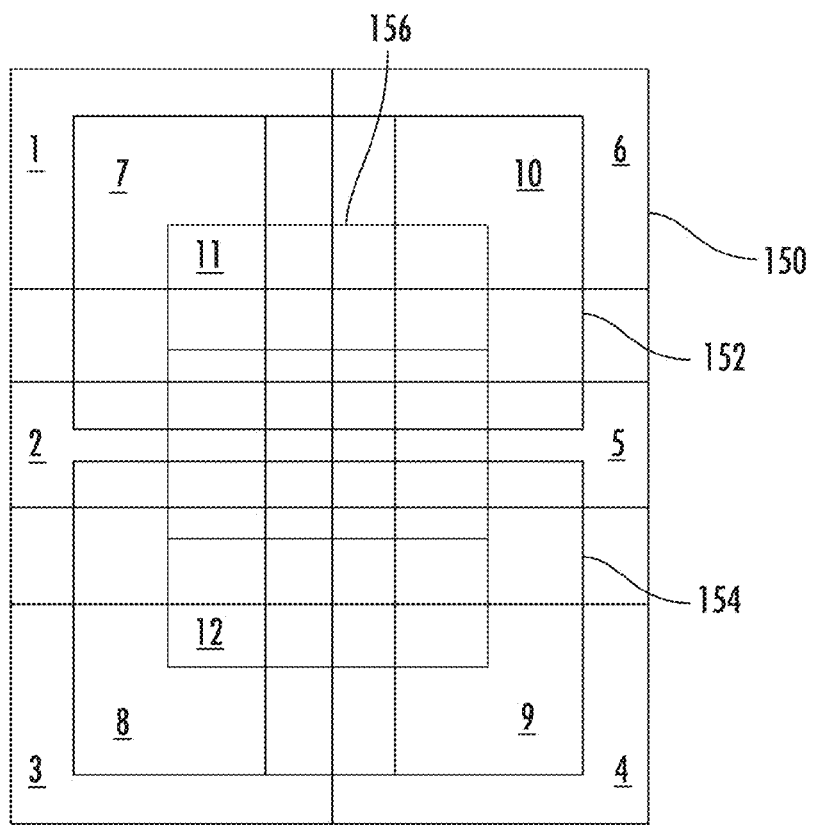
FIG. 4 depicts a plurality of overlapping non-conductive sheets that can be used to perform a plurality of coil property measurements with a single coil at a plurality of discrete locations relative to the target area according to example embodiments of the present disclosure.

One example technique for maintaining accurate position information for each coil property measurement includes performing the coil property measurement at a plurality of predefined locations relative to the target area. FIG. 4 depicts one example technique for performing a plurality of coil property measurements using a hand held coil device according to example aspects of the present disclosure.

More particularly, one or more non-conductive sheets having a known thickness can be overlaid on the target area of the patient. For instance, a first non-conductive sheet 150 can be placed over the target area. As shown, the first non-conductive sheet 150 includes a plurality of indicia (e.g. "1", "2", "3", "4", "5", "6" etc.) directing the medical professional as to where to perform each coil property measurement. The position information for each measurement can be determined from the location of the indicia and the depth or thickness of the non-conductive sheet 150.

Once the medical professional has performed the coil property measurements indicated by the indicia on the non-conductive sheet 150, one or more second non-conductive sheets can be placed over the first non-conductive sheet 150. For instance, second non-conductive sheet 152 and second non-conductive sheet 154 can be placed over the first non-conductive sheet 150. As shown, the second non-conductive sheet 152 and the second non-conductive sheet 154 can include a plurality of indicia (e.g. "7", "8", "9", "10") directing the medical professional as to where to perform the coil property measurement.

Once the medical professional has performed the coil property measurements indicated by the indicia on second non-conductive sheets 152 and 154, one or more third non-conductive sheets can be placed over the second non-conductive sheet 152 and 154. For instance, a third non-conductive sheet 156 can be placed over the second non-conductive sheets 152 and 154. As shown, the third non-conductive sheet 156 can include a plurality of indicia (e.g. "11" "12") directing the medical professional where to perform the coil property measurement. This process can be repeated for as many coil property measurements as desired to perform a plurality of coil property measurements with the single coil at a plurality of discrete locations relative to the target area.

The above example is discussed with reference to a plurality of non-conductive sheets for purposes of illustration and discussion. Those of ordinary skill in the art, using the disclosures provided herein, will understand that the above technique can be implemented using a single or multiple non-conductive sheets. For instance, indicia "1"-"12" of FIG. 4 can be located on a single non-conductive sheet.

Referring back to FIG. 1 at (106), the method (100) includes processing the coil property measurements to generate an image of the target area. For instance, a model defining a relationship between coil property measurements obtained by a single coil and the conductivity distribution of the target area can be accessed. A three-dimensional conductivity map of the target can be generated using the model based at least in part on the plurality of coil property measurements. One or more images of the conductivity distribution of the target area can be generated from the three-dimensional conductivity map. One example method for processing the plurality of coil property measurements to generate the image of the conductivity distribution of the target area will be discussed in more detail below with reference to FIG. 11.

Referring to FIG. 1 at (108), the method includes outputting the image of the target area for assessment of a health condition. For example, the image can be printed on a printing device on a suitable tangible medium for inspection and analysis by a medical professional. As another example, the image can be presented on a display device for inspection and analysis by a medical professional.

Figure 5:
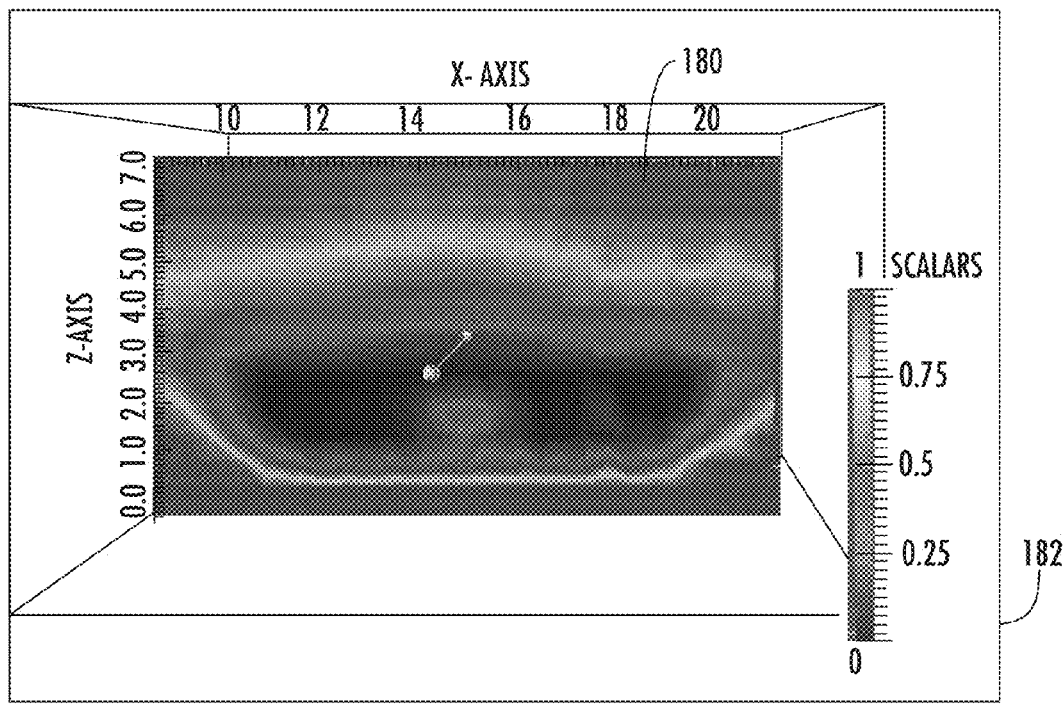
FIGS. 5-6 depict example images of a conductivity distribution generated according to example embodiments of the present disclosure.

FIG. 5 depicts one example image 180 of a conductivity distribution of a target area that can be generated from a plurality of coil property measurements using a single coil according to example embodiments of the present disclosure. The image 180 provides a transverse view of a spinal column of a patient, transecting and revealing the spinal canal. The image 180 plots conductivity distribution along x-, y-, and z-axis in units of centimeters. The image 180 includes a scale 182 indicative of grey scale colors associated with varying degrees of conductivity in units of S/m. As shown, the image 180 shows the contrasting conductivity of regions of human tissue in the spinal region.

Figure 6:
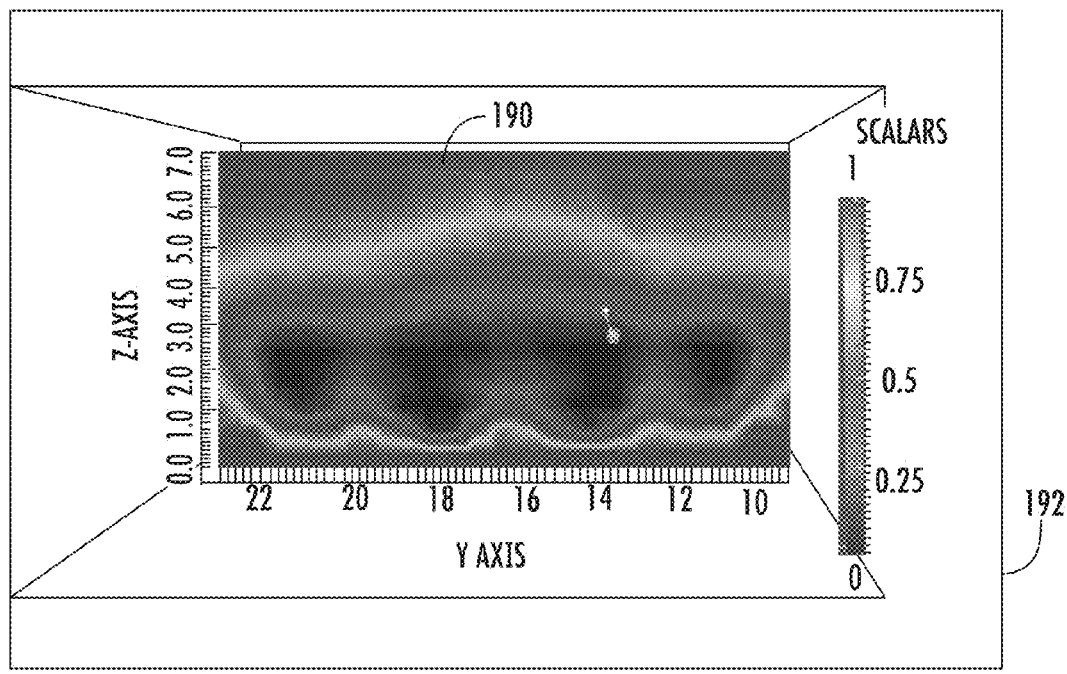

FIG. 6 depicts another example image 190 that can be generated from a plurality of coil property measurements using a single coil according to example embodiments of the present disclosure. The image 190 provides a sagittal view of the spinal region of a patient, parallel to and offset from the spinal column showing either ribs or transverse vertebral processes. The image 180 plots conductivity distribution along x-, y-, and z-axis in units of centimeters. The image 190 includes a scale 192 indicative of grey scale colors associated with varying degrees of conductivity of the target area in units of S/m. As shown, the image 190 shows the contrasting conductivity of regions of human tissue in the spinal region and can provide an image of the spinal region of the patient. This slice transects and reveals the structure associated with the connection of ribs to transverse processes of the vertebrae. The images 180 and 190, together with other images, can provide varying images of the spinal region of the patient for assessment of a health condition and other purposes.

One example application for assessing a health condition using single coil magnetic induction tomography imaging techniques can include using the images generated according to example aspects of the present disclosure to identify cancerous tissue in the target area. More particularly, cancerous tissue can be known to exhibit elevated electrical conductivity, due to angiogenesis. An image of the conductivity distribution of a target area can be particularly useful in identifying cancerous tissue in internal organs, such as the pancreas. Identification of cancer in breast tissue can be a particularly suitable application of single coil magnetic induction tomography as fatty tissue within the breast can exhibit a very low conductivity. Cancerous tissue in the breast can be significantly more conductive than the fatty tissue and can be expected to stand out in an image of the conductivity distribution of the tissue.

Another example application for assessing a health condition using single coil magnetic induction tomography imaging techniques can include using the images generated according to example aspects of the present disclosure to assess a burn condition of a patient. Burns can be classified as first degree, second degree, third degree, and fourth degree depending on the level of severity of the burn. First degree burns typically only include the outer layer of skin while more severe third degree burns can actually burn the skin away. Fourth degree burns can remove tissue down to the bone. With all burns there is some change in the physical properties of the skin and underlying tissues. For instance, there can be destroyed fat layers, fluid accumulation, altered blood flow, etc. Burns can also exhibit different characteristics based on the mechanism of injury (temperature, duration, location, etc.). As an example, sunburn may be widespread but not very deep while an electrical burn may present mostly below the skin.

Images of the target area generated according to example aspects of the present disclosure can be used early in treatment of burns, perhaps during transport, to identify the severity, type, and depth of a burn to insure proper treatment is given. More particularly, the images can be analyzed to identify changes in physical properties of the skin through identification of craters for deep burns or through identification of gaps for unseen damage beneath the skin. Accumulation of fluid, loss of blood flow, charred tissue, missing tissue, etc., can also be identified from the images of the conductivity distribution of the target area.

Another example application for assessing a health condition using single coil magnetic induction tomography imaging techniques can include using the images generated according to example aspects of the present disclosure to assess the presence of peripheral artery disease. Due to the insulating nature of small blood vessels, tissue conductivity has been shown to decrease when blood vessels are dilated and to increase when blood vessels contract. According to aspects of the present disclosure, images of a conductivity distribution of a target area can be generated in combination with intentionally inducing dilation or constriction of the blood vessels in the target area. The images can be analyzed to reveal the resilience of the vasculature. For example, a healthy individual with normal blood pressure can exhibit about a 0.5 S/m increase in conductivity when an arm or leg is elevated for a short period of time. An individual that does not exhibit such an increase can show signs of a stiffening of the blood vessels.

The above example applications of single coil magnetic induction tomography imaging are provided for purposes of illustration and discussion. Those of ordinary skill in the art, using the disclosures provided herein, will understand that single coil magnetic induction tomography imaging according to example aspects of the present disclosure can be used to assess a variety of health conditions of a patient without deviating from the scope of the present disclosure.

Example Systems for Magnetic Induction Tomography Imaging

FIG. 7 depicts an example system 200 for magnetic induction tomography imaging of a specimen 210, such as a human tissue specimen. The system 200 includes a coil device 220 having a single coil 225 for obtaining coil property measurements for magnetic induction tomography imaging according to example aspects of the present disclosure. The coil 225 can be a single coil having a plurality of concentric conductive loops disposed in one or more planes on a printed circuit board. One example coil design for magnetic induction tomography imaging according to example aspects of the present disclosure will be discussed in more detail below with reference to FIGS. 8 and 9 below.

The coil device 220 of FIG. 7 can include an RF energy source (e.g. an oscillator circuit) configured to energize the coil 225 with RF energy at a set frequency (e.g. 12.5 MHz) when the coil 225 is placed adjacent to the specimen 210. The energized coil 225 can generate magnetic fields, which can induce eddy currents in the specimen 210. These induced eddy currents in the specimen can cause a coil loss (e.g. a change in impedance) of the coil 225. The coil device 220 can include circuitry (e.g. a measurement circuit) for determining the coil loss associated with the coil 225 during a coil property measurement at a particular location relative to the specimen 210.

Coil property measurements can be obtained using the single coil 225 of the coil device 220 while the coil device 220 is positioned at a variety of different locations and orientations relative to the specimen 210. The collected coil property measurements can be provided to the computing system 240 where the coil property measurements can be analyzed to generate a three-dimensional electromagnetic property map of the specimen 210, such as a three-dimensional conductivity map or a three-dimensional permittivity map of the specimen 210.

In some particular implementations, the coil device 220 can be mounted to a translation device 230. The translation device 230 can be a robotic device controlled, for instance, by the computing system 240 or other suitable control device, to translate the coil device 220 along x-, y-, and z-axes relative to the specimen 210 in order to position the coil 225 at a plurality of different discrete locations relative to the specimen 210. The coil device 220 can be controlled (e.g. by the computing system 240) to obtain a coil property measurement using the coil 225 at each of the plurality of discrete locations.

Alternatively, the coil device 220 can be manually positioned at the plurality of discrete locations for performance of the coil property measurement. For instance, a medical professional can manually position a hand held coil device 220 relative to the specimen 210 to obtain coil property measurements at a plurality of discrete locations relative to the specimen 210.

To generate an accurate three-dimensional electromagnetic property map of the specimen 210, position data needs to be associated with each of the obtained coil property measurements. The position data can be indicative of the position (e.g. as defined by an x-axis, y-axis, and a z-axis relative to the specimen 210) of the coil 225 as well as an orientation of the coil 225 (e.g. a tilt angle relative to the specimen 210). When using a translation device 230 to position the coil 225, the position and orientation of the coil 225 can be determined based at least in part on positioning control commands that control the translation device 230 to be positioned at the plurality of discrete locations.

In one embodiment of the present disclosure, images captured by a camera 235 positioned above the specimen 210 and the coil device 220 to can be processed in conjunction with signals from various sensors associated with the coil device 220 to determine the position data for each coil property measurement. More particularly, the coil device 220 can include one or more motion sensors 226 (e.g. a three-axis accelerometer, gyroscope, and/or other motion sensors) and a depth sensor 228. The orientation of the single coil 225 relative to the surface can be determined using the signals from the motion sensors 226. For instance, signals from a three-axis accelerometer can be used to determine the orientation of the single coil 225 during a coil property measurement.

The depth sensor 228 can be used to determine the distance from the single coil to the specimen 210 (e.g. the position along the z-axis). The depth sensor 228 can include one or more devices configured to determine the location of the coil 225 relative to a surface. For instance, the depth sensor 228 can include one or more laser sensor devices and/or acoustic location sensors. In another implementation, the depth sensor 228 can include one or more cameras configured to capture images of the specimen 210. The images can be processed to determine depth to the specimen 210 using, for instance, structure-from-motion techniques.

Images captured by the camera 235 can be used to determine the position of the coil 225 along the x-axis and y-axis. More particularly, the coil device 220 can also include a graphic located on a surface of the coil device 220. As the plurality of coil property measurements are performed, the image capture device 235 can capture images of the graphic. The images can be provided to the computing system 240, which can process the images based on the location of the graphic to determine the position along the x-axis and y-axis relative to the specimen 210. In particular implementations, the camera 235 can include a telecentric lens to reduce error resulting from parallax effects.

The computing system 240 can receive the coil property measurements, together with coil location and orientation data, and can process the data to generate a three-dimensional electromagnetic property map of the specimen 210. The computing system 240 can include one or more computing devices, such as one or more of a desktop, laptop, server, mobile device, display with one or more processors, or other suitable computing device having one or more processors and one or more memory devices. The computing system 240 can be implemented using one or more networked computers (e.g., in a cluster or other distributed computing system). For instance, the computing system 240 can be in communication with one or more remote devices 260 (e.g. over a wired or wireless connection or network).

The computing system 240 includes one or more processors 242 and one or more memory devices 244. The one or more processors 242 can include any suitable processing device, such as a microprocessor, microcontroller, integrated circuit or other suitable processing device. The memory devices 244 can include single or multiple portions of one or more varieties of tangible, non-transitory computer-readable media, including, but not limited to, RAM, ROM, hard drives, flash drives, optical media, magnetic media or other memory devices. The computing system 240 can further include one or more input devices 262 (e.g. keyboard, mouse, touchscreen, touchpad, microphone, etc.) and one or more output devices 264 (e.g. display, speakers, etc.).

The memory devices 244 can store instructions 246 that when executed by the one or more processors 242 cause the one or more processors 242 to perform operations. The computing device 240 can be adapted to function as a special-purpose machine providing desired functionality by accessing the instructions 246. The instructions 246 can be implemented in hardware or in software. When software is used, any suitable programming, scripting, or other type of language or combinations of languages may be used to implement the teachings contained herein.

As illustrated, the memory devices 244 can store instructions 246 that when executed by the one or more processors 242 cause the one or more processors 242 to implement a magnetic induction tomography ("MIT") module 248. The MIT module 248 can be configured to implement one or more of the methods disclosed herein for magnetic induction tomography imaging using a single coil, such as the method disclosed in FIG. 11.

The one or more memory devices 244 of FIG. 7 can also store data, such as coil property measurements, position data, three-dimensional electromagnetic property maps, and other data. As shown, the one or more memory devices 244 can store data associated with an analytical model 250. The analytical model 250 can define a relationship between coil property measurements obtained by a single coil and an electromagnetic property distribution of the specimen 210. Features of an example analytical model will be discussed in more detail below.

MIT module 248 may be configured to receive input data from input device 262, from coil device 220, from translation device 230, from data that is stored in the one or more memory devices 244, or other sources. The MIT module 248 can then analyze such data in accordance with the disclosed methods, and provide useable output such as three-dimensional electromagnetic property maps to a user via output device 264. Analysis may alternatively be implemented by one or more remote device(s) 260.

The technology discussed herein makes reference to computing systems, servers, databases, software applications, and other computer-based systems, as well as actions taken and information sent to and from such systems. One of ordinary skill in the art, using the disclosures provided herein, will recognize that the inherent flexibility of computer-based systems allows for a great variety of possible configurations, combinations, and divisions of tasks and functionality between and among components. For instance, processes discussed herein may be implemented using a single computing device or multiple computing devices working in combination. Databases and applications may be implemented on a single system or distributed across multiple systems. Distributed components may operate sequentially or in parallel.

Example Quantitative Analytical Model for a Single Coil

An example quantitative analytical model for obtaining a three-dimensional conductivity map from a plurality of coil property measurements obtained by a single coil will now be set forth. The quantitative model is developed for an arbitrary conductivity distribution, but with permittivity and magnetic permeability treated as spatially uniform. The quantitative analytical model was developed for a coil geometry that includes a plurality of concentric circular loops, all lying within a common plane and connected in series, with the transient current considered to have the same value at all points along the loops. A conductivity distribution is permitted to vary arbitrarily in space while a solution for the electric field is pursued with a limit of small conductivity (<10 S/m). Charge free conditions are assumed to hold, whereby the electrical field is considered to have zero divergence. Under these conditions, fields are due only to external and eddy currents.

The quantitative analytical model can correlate a change in the real part of impedance (e.g. ohmic loss) of the coil with various parameters, including the conductivity distribution of the specimen, the position and orientation of the single coil relative to the specimen, coil geometry (e.g. the radius of each of the plurality of concentric conductive loops) and other parameters. One example model is provided below:

$$-\delta Z_{re} = \frac{\mu^2 \omega^2}{4\pi^2} \sum_{j,k} \sqrt{\rho_j \rho_k} \int d^3 x \frac{\vec{\sigma}(\vec{r})}{\rho} Q_{\frac{1}{2}}(\eta_j) Q_{\frac{1}{2}}(\eta_k)$$

$-\delta Z_{re}$ is the coil property measurement (e.g. the real part of the impedance loss of the coil). $\mu$ is the magnetic permeability in free space. $\omega$ is the excitation frequency of the coil. $\rho_k$ and $\rho_j$ are the radii of each conductive loop j and k for each interacting loop pair j,k. The function $Q_{1/2}$ is known as a ring function or toroidal harmonic function, which has the argument $\eta_j$ and $\eta_k$ as shown here:

$$\eta_j = \frac{\rho^2 + \rho_j^2 + z^2}{2\rho\rho_j}$$

$$\eta_k = \frac{\rho^2 + \rho_k^2 + z^2}{2\rho\rho_k}$$

With reference to a coordinate system placed at the center of the concentric loops, such that loops all lie within the XY-plane, $\rho$ measures radial distance from coil axis to a point within the specimen while z measures distance from the coil plane to the same point within the specimen.

The model introduces electrical conductivity $\breve{\sigma}(\vec{r})$ as a function of position. The integrals can be evaluated using a finite element mesh (e.g. with tetrahedral elements) to generate the conductivity distribution for a plurality of coil property measurements as will be discussed in more detail below.

Example Coil Device for Magnetic Induction Tomography Imaging

As demonstrated above, the inventors have developed a quantitative analytical model that defines a relationship between a plurality of coil property measurements obtained by a single coil having a plurality of concentric conductive loops connected in series and a conductivity distribution of a specimen. An example coil design that approximates the coil contemplated by the example quantitative model will now be set forth A coil according to example aspects of the present disclosure can include a plurality of concentric conductive loops arranged in two-planes on a multilayer printed circuit board. The plurality of concentric conductive loops can include a plurality of first concentric conductive loops located within a first plane and a plurality of second concentric conductive loops located in a second plane. The second plane can be spaced apart from the first plane by a plane separation distance. The plane separation distance can be selected such that the coil approximates the single plane coil contemplated in the example quantitative analytical model for magnetic induction tomography imaging disclosed herein.

In addition, the plurality of conductive loops can be connected in series using a plurality of connection traces. The plurality of connection traces can be arranged so that the contribution to the fields generated by the connection traces can be reduced. In this manner, the coil according to example aspects of the present disclosure can exhibit behavior that approximates a plurality of circular loops arranged concentric to one another and located in the same plane.

Figure 8:
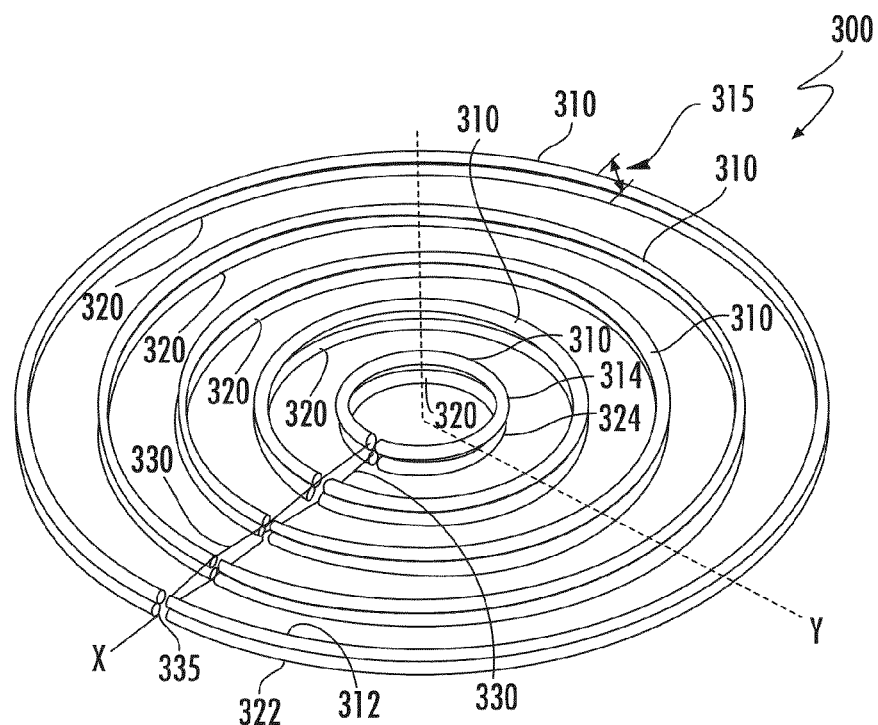
FIG. 8 depicts an example coil for magnetic induction tomography imaging according to example embodiments of the present disclosure.

FIG. 8 depicts an example coil 300 used for magnetic induction tomography imaging according to example aspects of the present disclosure. As shown, the coil 300 includes ten concentric conductive loops. More particularly, the coil 300 includes five first concentric conductive loops 310 disposed in a first plane and five second concentric conductive loops 320 disposed in a second plane. The first and second concentric conductive loops 310 and 320 can be 1 mm or 0.5 mm copper traces on a multilayer printed circuit board. In one example implementation, the radii of the five concentric conductive loops in either plane are set at about 4 mm, 8 mm, 12 mm, 16 mm, and 20 mm respectively. Other suitable dimensions and spacing can be used without deviating from the scope of the present disclosure.

As shown, each of the plurality of first concentric conductive loops 310 is disposed such that it overlaps one of the plurality of second concentric conductive loops 320. In addition, the first concentric conductive loops 310 and the second concentric conductive loops 320 can be separated by a plane separation distance 315. The plane separation distance 315 can be selected such that the coil 300 approximates a single plane of concentric loops as contemplated by the quantitative analytical model. For instance, the plane separation distance can be in the range of about 0.2 mm to about 0.7 mm, such as about 0.5 mm.

The plurality of first conductive loops 310 can include a first innermost conductive loop 314. The first innermost conductive loop 314 can be coupled to an RF energy source. The plurality of second conductive loops 320 can include a second innermost conductive loop 324. The second innermost conductive loop 324 can be coupled to a reference node (e.g. a ground node or common node).

The coil 300 further includes a plurality of connection traces 330 that are used to connect the first concentric conductive loops 310 and the second concentric conductive loops 320 in series. More particularly, the connection traces 330 couple the plurality of first concentric conductive loops 310 in series with one another and can couple the plurality of second concentric conductive loops 320 in series with one another. The connection traces 330 can also include a connection trace 235 that couples the outermost first concentric conductive loop 312 with the outermost second concentric conductive loop 314 in series.

Figure 9:
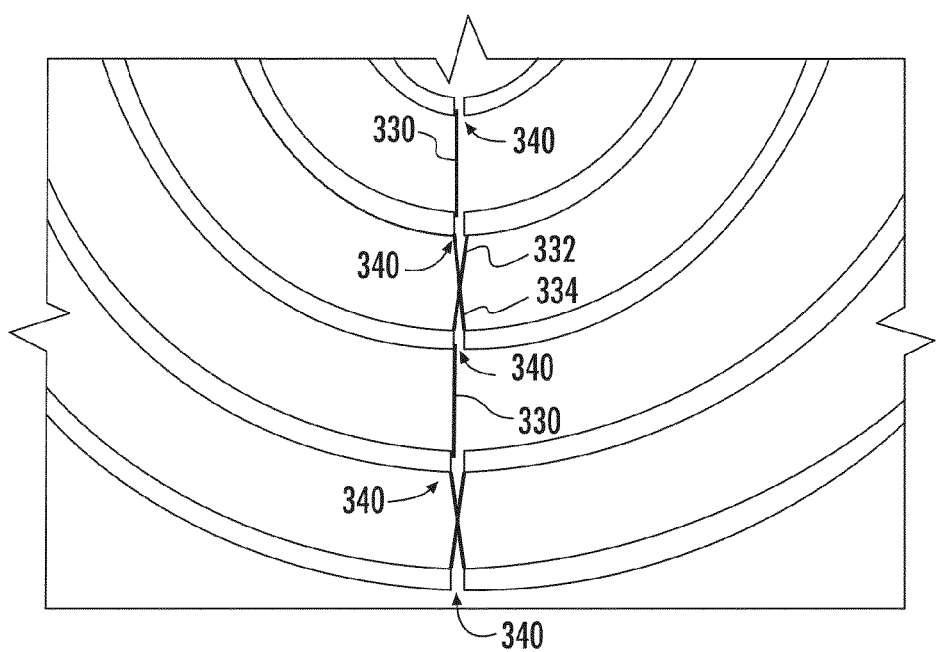
FIG. 9 depicts example connection traces for a coil for magnetic induction tomography imaging according to example embodiments of the present disclosure.

As shown in more detail in FIG. 9, the connection traces 330 can be arranged such that fields emanating from the connection traces oppose each other. More particularly, the connection traces 330 can be radially aligned such that a current flow of one of the plurality of connection traces located in the first plane is opposite to a current flow of one of the plurality of connection traces located in the second plane. For instance, referring to FIG. 9, connection trace 332 arranged in the first plane can be nearly radially aligned with connection trace 334 arranged in the second plane. A current flowing in connection trace 332 can be opposite to the current flowing in connection trace 234 such that fields generated by the connection traces 332 and 334 oppose or cancel each other.

As further illustrated in FIG. 9, each of the plurality of first conductive loops 210 and the second conductive loops 320 can include a gap 340 to facilitate connection of the conductive loops using the connection traces 330. Each gap can be in the range of about 0.2 mm to about 0.7 mm, such as about 0.5 mm.

The gaps 340 can be offset from one another to facilitate connection of the plurality of concentric conductive loops 310 and 320 in series. For instance, a gap associated with one of the plurality of first concentric conductive loops 310 can be offset from a gap associated with another of the plurality of first concentric conductive loops 310. Similarly, a gap associated with one of the plurality of second concentric conductive loops 320 can be offset from a gap associated with another of the plurality of second concentric conductive loops 320. A gap associated with one of the first concentric conductive loops 310 can also be offset from a gap associated with one of the plurality of second concentric conductive loops 320. Gaps that are offset may not be along the same axis associated with the coil 300.

As shown in the experimental results that follow, the coil 300 of FIGS. 8 and 9 can provide a good approximation of the coil contemplated by the quantitative analytical model for magnetic induction tomography imaging. In this way, coil property measurements using the coil 300 can be used to generate three-dimensional electromagnetic property maps of specimens of interest (e.g. human tissue specimens).

Example Circuit for Obtaining Coil property measurements

Figure 10:
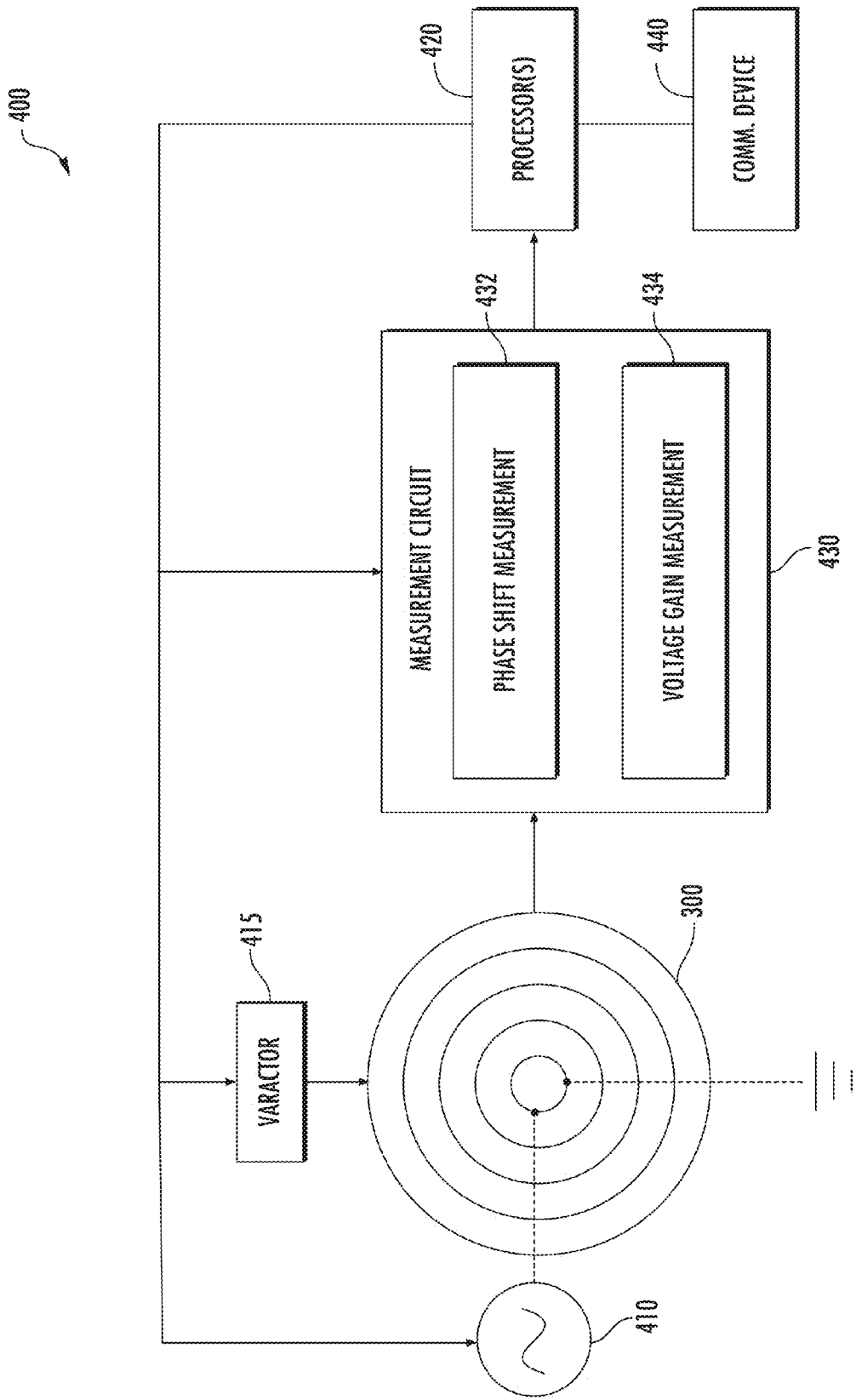
FIG. 10 depicts a block diagram of an example circuit associated with a coil used for magnetic induction tomography imaging according to example embodiments of the present disclosure.

FIG. 10 depicts a diagram of an example circuit 400 that can be used to obtain coil property measurements using the coil 300 of FIGS. 8 and 9. As shown, the circuit 400 of FIG. 10 includes an RF energy source 410 (e.g. an oscillator circuit) configured to energize the coil 300 with RF energy. The RF energy source 410 can be a fixed frequency crystal oscillator configured to apply RF energy at a fixed frequency to the coil 300. The fixed frequency can be, for instance, about 12.5 MHz. In one example embodiment, the RF energy source 410 can be coupled to an innermost concentric conductive loop of the plurality of first concentric conductive loops of the coil 300. The innermost concentric conductive loop of the plurality of second concentric conductive loops of the coil 300 can be coupled to a reference node (e.g. common or ground).

The circuit 400 can include one or more processors 420 to control various aspects of the circuit 400 as well as to process information obtained by the circuit 400 (e.g. information obtained by measurement circuit 430). The one or more processors 420 can include any suitable processing device, such as digital signal processor, microprocessor, microcontroller, integrated circuit or other suitable processing device.

The one or more processors 420 can be configured to control various components of the circuit 400 in order to capture a coil loss measurement using the coil 300. For instance, the one or more processors 420 can control a varactor 415 coupled in parallel with the coil 300 so as to drive the coil 300 to resonance or near resonance when the coil 300 is positioned adjacent a specimen for a coil property measurement. The one or more processors 420 can also control the measurement circuit 430 to obtain a coil property measurement when the coil 300 is positioned adjacent the specimen.

The measurement circuit 430 can be configured to obtain coil property measurements with the coil 300. The coil property measurements can be indicative of coil losses of the coil 300 resulting from eddy currents induced in the specimen. In one implementation, the measurement circuit 430 can be configured to measure the real part of admittance changes of the coil 300. The real part of admittance changes of the coil 300 can be converted to real part of impedance changes of the coil 300 as the inverse of admittance for purposes of the analytical model.

The admittance of the coil 300 can be measured in a variety of ways. In one embodiment, the measurement circuit 430 measures the admittance using a phase shift measurement circuit 432 and a voltage gain measurement circuit 434. For instance, the measurement circuit 430 can include an AD8302 phase and gain detector from Analog Devices. The phase shift measurement circuit 432 can measure the phase shift between current and voltage associated with the coil 300. The voltage gain measurement circuit 434 can measure the ratio of the voltage across the coil 300 with a voltage of a sense resistor coupled in series with the coil 300. The admittance of the coil 300 can be derived (e.g. by the one or more processors 420) based on the phase and gain of the coil 300 as obtained by the measurement circuit 430.

Once the coil property measurements have been obtained, the one or more processors 420 can store the coil property measurements, for instance, in a memory device. The one or more processors 420 can also communicate the coil property measurements to one or more remote devices for processing to generate a three-dimensional electromagnetic property map of the specimen using communication device 440. Communication device 440 can include any suitable interface or device for communicating information to a remote device over wired or wireless connections and/or networks.

Example Methods for Magnetic Induction
Tomography Imaging

Figure 11:
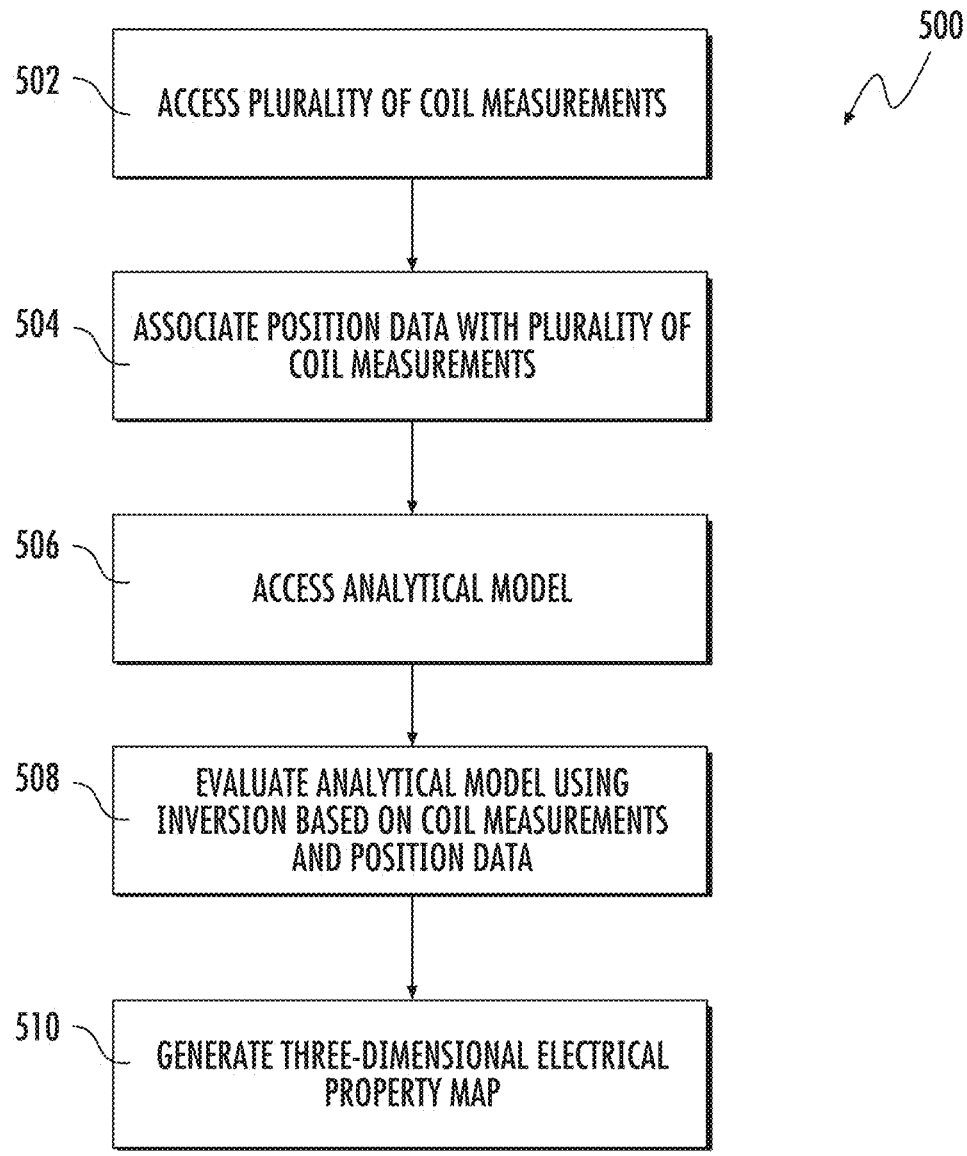
FIG. 11 depicts a process flow diagram of an example method according to example embodiments of the present disclosure.

FIG. 11 depicts a process flow diagram of an example method (500) for magnetic induction tomography imaging according to example aspects of the present disclosure. The method (500) can be implemented by one or more computing devices, such as one or more computing devices of the computing system 240 depicted in FIG. 7. In addition, FIG. 11 depicts steps performed in a particular order for purposes of illustration and discussion. Those of ordinary skill in the art, using the disclosures provided herein, will understand that the steps of any of the methods disclosed herein can be modified, omitted, rearranged, adapted, or expanded in various ways without deviating from the scope of the present disclosure.

At (502), the method can include accessing a plurality of coil property measurements performed using a single coil at a plurality of different discrete locations relative to the specimen. For instance, the plurality of coil property measurements can be accessed from a memory device or can be received from a coil device having a single coil configured for obtaining the coil property measurements. The coil property measurements can be coil loss measurements captured by a single coil when the single coil is energized with RF energy and placed adjacent a specimen at one of the plurality of discrete locations.

In one implementation, the single coil can include a plurality of concentric conductive loops. For instance, the single coil can have a plurality of first concentric conductive loops arranged in a first plane and a plurality of second concentric conductive loops arranged in a second plane. The plurality of concentric conductive loops can be connected using connection traces arranged so as to have a reduced impact on the field created by the coil. For example, the single coil can have the coil geometry of the coil 300 depicted in FIGS. 8 and 9.

The coil property measurements can be performed at a plurality of discrete positions relative to the specimen. Each coil property measurement can be taken at a different discrete position relative to the specimen. A greater number of coil property measurements can lead to increased accuracy in generating a three-dimensional electromagnetic property map from the coil property measurements.

In a particular embodiment, the coil property measurements can include a plurality of different data sets of coil property measurements. Each of the data sets can be built by conducting a plurality of coil property measurements using a single coil. The single coil can be different for each data set. For instance, each data set can be associated with a single coil having a different overall size and/or outer diameter, relative to any of the other single coils associated with the other data sets. The data sets can be obtained at different times. The data sets can be collectively processed according to example aspects of the present disclosure to generate a three-dimensional electrical property distribution of the specimen as discussed below.

At (504) of FIG. 11, the method includes associating position data with each of the plurality of coil property measurements. The position data for each coil property measurement can be indicative of the position and orientation of the single coil relative to the specimen when the coil property measurement was performed. The position data can be associated with each coil property measurement, for instance, in a memory device of a computing system.

The position data can be obtained in a variety of ways. In one implementation, the position data can be obtained for each measurement from data associated with a translation device used to position the single coil relative to the specimen at the plurality of discrete locations relative to the specimen. For example, the translation device can be controlled to position the single coil at a plurality of defined locations relative to the specimen. The position data can be determined from these defined locations.

Signals from one or more sensors (e.g. one or more motion sensors and one or more depth sensors) associated with the single coil can be also used to determine the position data for a coil property measurement. Images can also be captured of the coil device containing the single coil as the plurality of coil property measurements is performed. The position of the single coil can be determined for instance, based on the position of a graphic on the surface of the coil device depicted in the images.

At (506), the method includes accessing an analytical model defining a relationship between coil property measurements obtained by the single coil and an electromagnetic property of the specimen. For instance, the analytical model can be accessed, for instance, from a memory device. In one particular implementation, the analytical model correlates a change in impedance of a single coil having a plurality of concentric conductive loops with a conductivity distribution of the specimen. More particularly, the analytical model can correlate the change in impedance of a single coil with a variety of parameters. The parameters can include the conductivity distribution of the specimen, the position and orientation associated with each coil loss measurement, and the geometry of the coil (e.g. the radius of each of the concentric conductive loops).

At (508), the method includes evaluating the analytical model based on the plurality of coil property measurements and associated position data. More particularly, an inversion can be performed using the model to determine a conductivity distribution that most closely leads to the plurality of obtained coil property measurements. In one example aspect, the inversion can be performed by discretizing the specimen into a finite element mesh. The finite element mesh can include a plurality of polygonal elements, such as tetrahedral elements. The shape and resolution of the finite element mesh can be tailored to the specimen being analyzed. As a matter of practicality, the coil location data can be used to avoid meshing those regions of space visited by the coil, improving efficiency. Once the finite element mesh has been generated for the specimen, a conductivity distribution for the finite element mesh can be computed using a non-linear or constrained least squares solver.

More particularly, a plurality of candidate electromagnetic property distributions can be computed for the finite element mesh. Each of these candidate electromagnetic property distributions can be evaluated using a cost function, such as the root mean square error. The cost function can assign a cost to each candidate electromagnetic property distribution based at least in part on the difference between the obtained coil property measurements and theoretical coil property measurements using the model. The candidate electromagnetic property distribution with the lowest cost can be selected as the electromagnetic property distribution for the specimen. Those of ordinary skill in the art, using the disclosures provided herein, will understand that other suitable techniques can be used to determine an electromagnetic property distribution using the analytical model without deviating from the scope of the present disclosure.

At (510), a three-dimensional electromagnetic property map can be generated based on the electromagnetic property distribution identified using the inversion algorithm. The three-dimensional property map can provide an electromagnetic property distribution (e.g. a conductivity distribution) for a plurality of three-dimensional points associated with the specimen. Two-dimensional views along cross-sections of the three-dimensional electromagnetic property map can then be captured and presented, for instance, on a display device. Three-dimensional views of the electromagnetic property map can also be generated, rotated, and presented, for instance, on a display device.

Experimental Results #1

Two coils having a coil geometry of the coil 300 depicted in FIGS. 8 and 9 were constructed. Coil "R" had a 1 mm trace width. Coil "S" had a 0.5 mm trace width. Each trace was built with 2 oz. copper. The traces on coil "R" had an equivalent circular wire diameter of 0.68 mm, equivalent in the sense of having identical perimeters. The traces on coil "S" had an equivalent circular wire diameter of 0.36 mm.

The coil was positioned at a plurality of discrete locations relative to a specimen including a 30 cm×30 cm×13 cm deep tank of aqueous KCl having known conductivity. Admittance change relative to free space was measured and then used to compute loss. This was then compared to theoretical losses computed using the quantitative analytical model discussed above.

Figure 12:
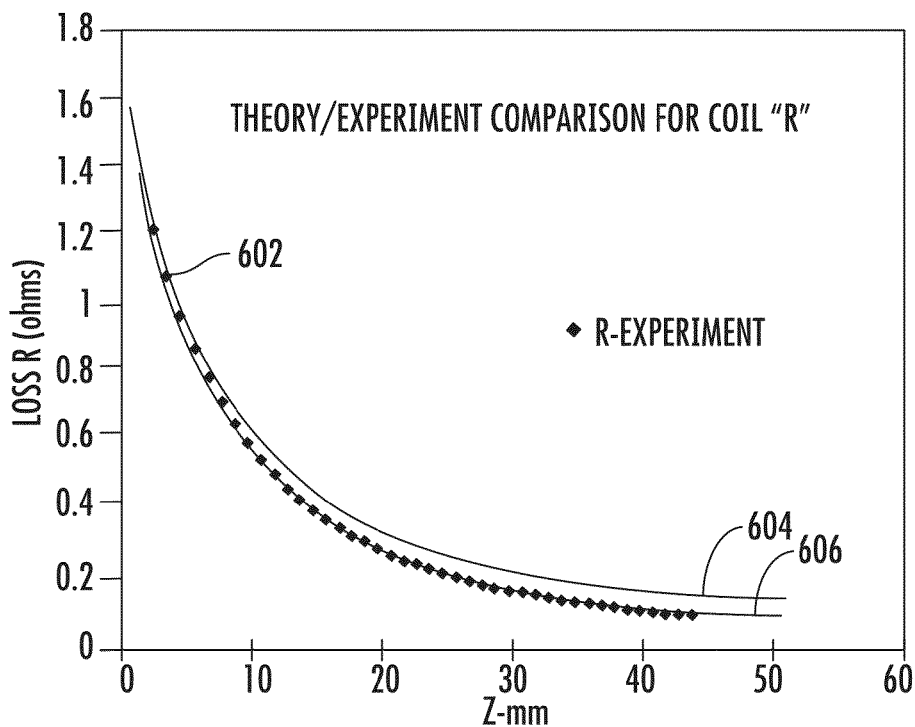
FIGS. 12 and 13 depict experimental results for coil property measurements obtained using an example coil according to example embodiments of the present disclosure.

FIG. 12 depicts a comparison of theoretical losses versus observed losses for coil "R". FIG. 12 plots depth from, or distance above, the specimen along the abscissa and coil losses along the ordinate. Curve 602 depicts the observed losses for coil "R". Curve 604 depicts theoretical losses for an infinite slab 13 cm thick. Curve 606 depicts theoretical losses for a finite slab.

Figure 13:
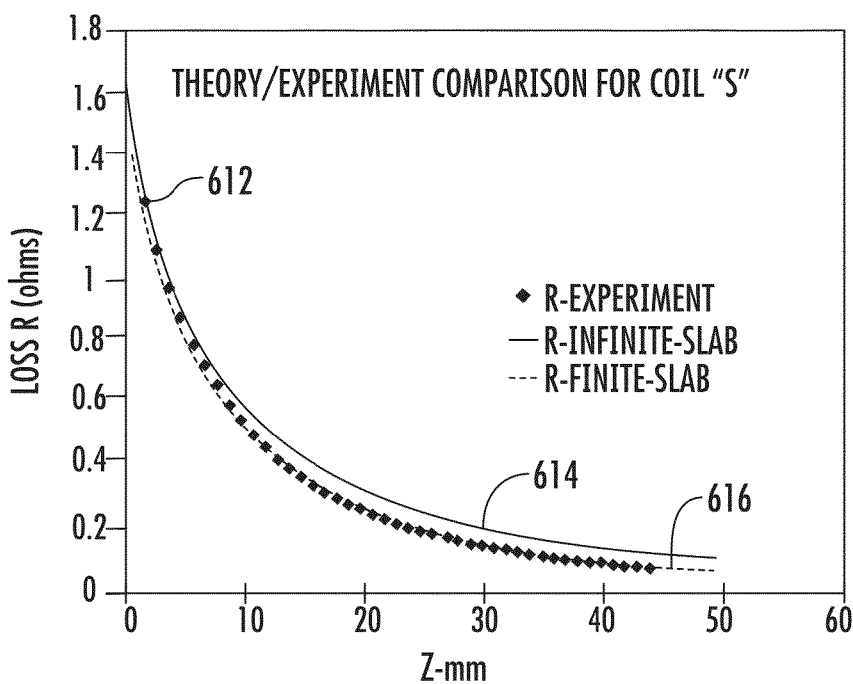

FIG. 13 depicts a comparison of theoretical losses versus observed losses for coil "S". FIG. 10 plots depth from, or distance above, the specimen along the abscissa and coil losses along the ordinate. Curve 612 depicts the observed losses for coil "S". Curve 614 depicts theoretical losses for an infinite slab 13 cm thick. Curve 616 depicts theoretical losses for a finite slab.

As demonstrated in FIGS. 12 and 13, coil property measurements obtained using the coil geometry of the coil 300 of FIGS. 8 and 9 closely track theoretical ohmic losses using the example quantitative analytical model disclosed herein. As a result the coil 300 of FIGS. 8 and 9 can be effectively used for magnetic induction tomography imaging using a single coil according to example aspects of the present disclosure.

Experimental Results #2

To test the example quantitative analytical model according to example aspects of the preset disclosure, a specimen including slab with dimensions 9 cm×9 cm square and 2 cm thick was subdivided into two layers. A finite element mesh was generated for the specimen consisting of 380 pentahedral elements and 342 nodes. Electrical conductivity is distributed over the mesh nodes varying in conductivity from 1.0 S/m near the corners to 3.0 S/m near the center. FIG. 13 shows the theoretical conductivity distribution 620 defined for the specimen according to the following:

$$\check{\sigma}(x, y) = 1 + \sin^2\left(\frac{x}{3}\right) + \sin^2\left(\frac{y}{3}\right)$$

Figure 14:
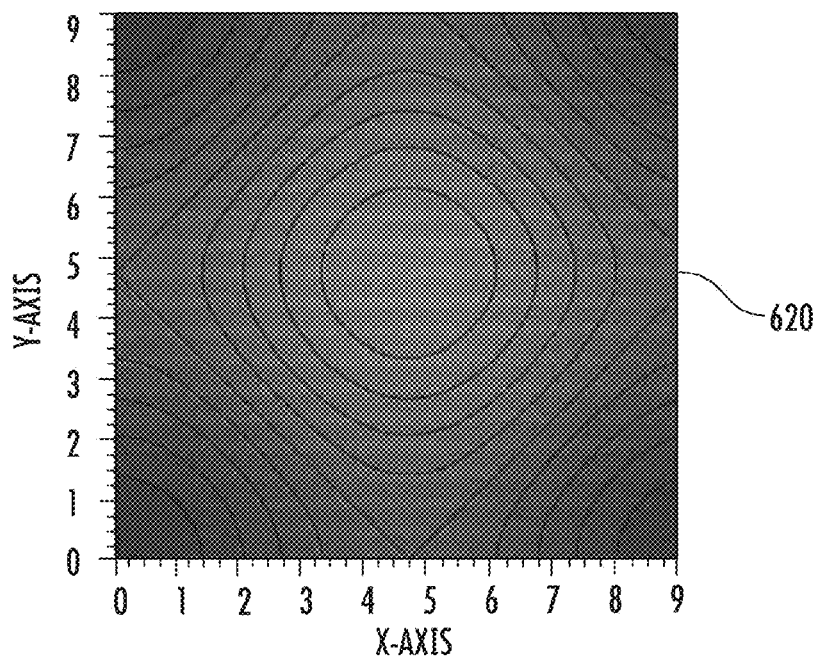
FIGS. 14 and 15 depict experimental results for coil property measurements obtained for a simulated conductivity distribution according to example embodiments of the present disclosure.
Figure 15:
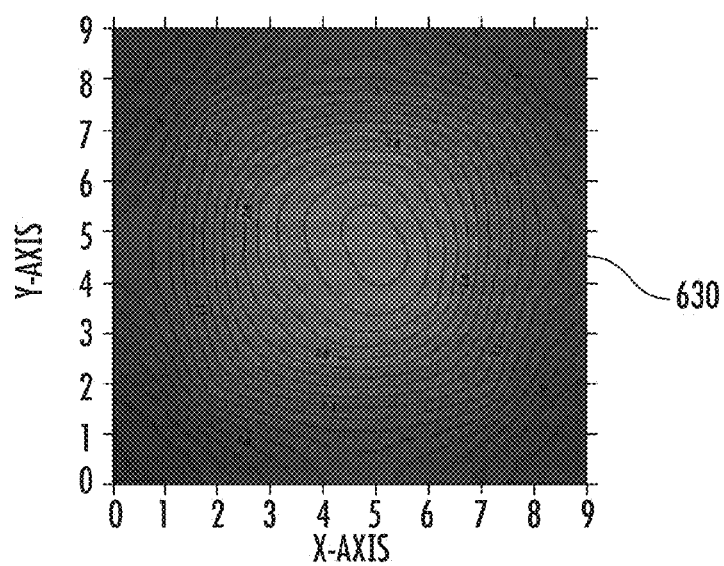

Nine virtual coil property measurements were simulated using a single coil at nine discrete coil positions. An inversion was performed using the quantitative analytical model based at least in part on the nine coil property measurements. FIG. 14 depicts the resulting three-dimensional conductivity map 630 determined using the inversion. As demonstrated, the three-dimensional conductivity map 630 approximates the true conductivity distribution 620 and is determined using only nine coil property measurements by a single coil at discrete positions relative to the specimen.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A method for assessing a health condition of a patient, the method comprising:
   identifying a target area on a patient for medical imaging;
   obtaining a plurality of coil property measurements of the target area using a single coil, the plurality of coil property measurements being performed with the single coil at a plurality of discrete locations relative to the target area;
   processing the plurality of coil property measurements to generate an image of the conductivity distribution of the target area using a model defining a relationship between coil property measurements obtained by the single coil at a plurality of different positions relative to the target area and a conductivity of the target area; and
   outputting the image for assessment of a health condition of the patient.

2. The method of claim 1, wherein the coil property measurement comprises a coil loss measurement indicative of a change in impedance of the single coil resulting from eddy currents induced in the target area when the single coil is placed adjacent to the target area and energized with radio frequency energy.

3. The method of claim 1, wherein at least a portion of the target area is obscured by bone tissue.

4. The method of claim 3, wherein the target area comprises at least a portion of a brain or spinal column.

5. The method of claim 1, wherein the target area is at a location at least partially occupied by a gas.

6. The method of claim 5, wherein the target area comprises one or more of a trachea, a lung, a stomach, or bowels.

7. The method of claim 1, wherein the method further comprises using the image to identify cancerous tissue.

8. The method of claim 7, wherein the target area comprises a breast or a pancreas.

9. The method of claim 1, wherein the method further comprises using the image to assess a burn condition of the patient.

10. The method of claim 1, wherein the plurality of coil property measurements are obtained using a hand held coil device, the hand held coil device comprising the single coil.

11. The method of claim 10, wherein the plurality of coil property measurements are obtained while the single coil is placed on one or more non-conductive sheets overlaying the specimen, the non-conductive sheets having indicia indicative of one or more of the discrete locations.

12. The method of claim 1, wherein the plurality of coil property measurements are obtained while the target area is pressed against an insulative plate, the single coil being positioned at the plurality of discrete locations on the other side of the insulative plate.

13. The method of claim 1, wherein the non-conductive plate has a shape adapted to accommodate the target area to facilitate immobilization of the target area.

14. The method of claim 1, wherein the plurality of coil property measurements are obtained while the patient is located on a table having a non-conductive surface, the single coil being disposed within a cavity located in the table.

15. The method of claim 1, wherein the table comprises one or more non-conductive supports to facilitate immobilization of the target area.

16. The method of claim 1, wherein the patient is a human patient.

17. A method for assessing a health condition of a patient, the method comprising:

identifying a target area on a patient for medical imaging;

obtaining a plurality of coil property measurements of the target area using a single coil of a magnetic induction tomography imaging system, the plurality of coil loss measurements being performed with the single coil at a plurality of discrete locations relative to the target area, the single coil comprising one or more concentric conductive loops arranged in one or more planes on a printed circuit board;

accessing a model defining a relationship between coil property measurements obtained by the single coil at a plurality of different positions relative to the target area and the conductivity distribution of the target area; and generating an image of the conductivity distribution of the target area from the plurality of coil property measurements based on the model; and outputting the image for assessment of a health condition of the patient.

18. The method of claim 17, wherein the plurality of coil property measurements are obtained using a hand held coil device, the hand held coil device comprising the single coil.

19. The method of claim 18, wherein the plurality of coil property measurements are obtained while the single coil is placed on one or more non-conductive sheets overlaying the specimen, the non-conductive sheets having indicia indicative of one or more of the discrete locations.

20. The method of claim 17, wherein the plurality of coil property measurements are obtained while the target area is pressed against an insulative plate, the single coil being positioned at the plurality of discrete locations on the other side of the insulative plate.

21. The method of claim 17, wherein the plurality of coil property measurements are obtained while the patient is located on a table having a non-conductive surface, the single coil being disposed within a cavity located in the table.

22. The method of claim 17, wherein the patient is a human patient.

* * * * *